US010434098B2

(12) United States Patent
Li et al.

(10) Patent No.: US 10,434,098 B2
(45) Date of Patent: Oct. 8, 2019

(54) DEUTERATED DEHYDROPHENYLAHISTIN COMPOUNDS AND PREPARATION METHOD THEREOF AND USE THEREOF IN PREPARATION OF ANTI-TUMOR DRUGS

(71) Applicant: MARINE BIOMEDICAL RESEARCH INSTITUTE OF QINGDAO CO., LTD., Shandong (CN)

(72) Inventors: Wenbao Li, Shandong (CN); Tianwen Sun, Shandong (CN); Shixiao Wang, Shandong (CN); Jianchun Zhao, Shandong (CN); Bing Cai, Shandong (CN); Huashi Guan, Shandong (CN)

(73) Assignee: MARINE BIOMEDICAL RESEARCH INSTITUTE OF QINGDAO CO., LTD., Shandong (CN)

( * ) Notice: Subject to any disclaimer, the term of this patent is extended or adjusted under 35 U.S.C. 154(b) by 0 days.

(21) Appl. No.: 15/579,429

(22) PCT Filed: May 27, 2016

(86) PCT No.: PCT/CN2016/083610
§ 371 (c)(1),
(2) Date: Dec. 4, 2017

(87) PCT Pub. No.: WO2016/192586
PCT Pub. Date: Dec. 8, 2016

(65) Prior Publication Data
US 2018/0140600 A1    May 24, 2018

(30) Foreign Application Priority Data
Jun. 2, 2015  (CN) .......................... 2015 1 0293269

(51) Int. Cl.
| C07D 233/64 | (2006.01) |
| C07D 403/06 | (2006.01) |
| A61K 31/496 | (2006.01) |
| C07B 59/00 | (2006.01) |
| A61P 35/00 | (2006.01) |

(52) U.S. Cl.
CPC ............ *A61K 31/496* (2013.01); *A61P 35/00* (2018.01); *C07B 59/00* (2013.01); *C07B 59/002* (2013.01); *C07D 233/64* (2013.01); *C07D 403/06* (2013.01)

(58) Field of Classification Search
CPC ............................ C07D 233/64; C07D 403/06
See application file for complete search history.

(56) References Cited

U.S. PATENT DOCUMENTS

2008/0221122 A1    9/2008    Palladine et al.

FOREIGN PATENT DOCUMENTS

| CN | 1684955 A | 10/2005 |
| WO | WO 95/26325 | * 10/1995 |
| WO | 2012/035436 A1 | 3/2012 |

OTHER PUBLICATIONS

International Search Report and Written Opinion for Application No. PCT/CN2016/083610 dated Aug. 19, 2016 (8 pages).
Blake et al., "Studies with Deuterated Drugs," Journal of Pharmaceutical Sciences, 1975; 64(3):367-391.
Carlstedt et al., "Biosynthesis of Deuterated Benzylpenicillins III: Relative Antibiotic Potency of Highly Deuterated Benzylpenicillin," Journal of Pharmaceutical Sciences, 1973; 62(5):856-857.
Vulliemoz et al., "Deuterated Halothane—Anesthetic Potency, Anticonvulsant Activity, and Effect on Cerebellar Cyclic Guanosine 3',5'-Monophosphate," Anesthesia & Analgesia, 1984; 63(5):495-8.

* cited by examiner

*Primary Examiner* — Bruck Kifle
(74) *Attorney, Agent, or Firm* — Michael Best & Friedrich LLP (57) ABSTRACT

Provided are a deuterium-substituted dehydrophenylahistin-like compound, preparation method thereof and use in a preparation of antitumor drugs. The deuterium-substituted dehydrophenylahistin-like compound has a structure of general formula (I), and a synthesis method thereof comprises: firstly conducting a condensation reaction of diacetyldiketopiperazine and an aldehyde intermediate a or a deuterated aldehyde compound b to form a heterocyclic compound c or a deuterium-containing heterocyclic compound d, which is then subjected to a condensation reaction with benzaldehyde and a deuterium-substituted benzaldehyde-like compound to form the deuterium-substituted dehydrophenylahistin-like compound. Also provided are a highly effective deuterated aldehyde intermediate with a high deuterium substitution rate and a deuterium-containing heterocycle intermediate, and a synthesis method thereof. An experiment shows that the deuterium-substituted dehydrophenylahistin-like compound provided by the present invention has an effect on tubulin depolymerization and can treat a refractory solid tumor or lymphoma. The present invention provides a method for researching and developing antitumor drugs of the related compound.

9 Claims, 2 Drawing Sheets

DEUTERATED DEHYDROPHENYLAHISTIN COMPOUNDS AND PREPARATION METHOD THEREOF AND USE THEREOF IN PREPARATION OF ANTI-TUMOR DRUGS

CROSS-REFERENCE TO RELATED APPLICATION(S)

This application is a national stage filing under 35 U.S.C. § 371 of International Application No. PCT/CN2016/083610, filed on May 27, 2016, which application claims the benefit of Chinese Patent Application No. 201510293269.8, filed on Jun. 2, 2015, the entire contents of each of which are fully incorporated herein by reference.

FIELD OF THE INVENTION

The invention belongs to the field of chemistry and medicine technology, and relates to a medicinal compound and its preparation method and use thereof, and particularly relates to deuterated dehydrophenylahistin compounds and a preparation method and use thereof in preparation of anti-tumor drugs.

BACKGROUND OF THE INVENTION

As everyone knows, angiogenesis is of vital importance to the growth and transfer of tumors; hence, the tumor vessel system has become a valuable tumor therapy target. Generally speaking, the anti-tumor drugs that target tumor vascular system mainly comprises an anti-angiogenic agent and a vascular disrupting agent (VDAs), in which the former can inhibit the growth of new tumor vessels, and the latter is used for targeting and destroying the existing vascular net that supplies oxygen and nutrients to tumor cells. The tumor vessel has an abnormal structure different from the normal vessel, its endothelial cells are fast proliferating, and the vascular wall gets thin and has high permeability, resulting in high blood stream resistance. VDAs can be selectively acted on the vascular endothelial cells of the tumors, interfering with its the binding site of adhesion and microtubule cytoskeleton, thereby affecting the migration, adhesion and proliferation of endothelial cells, resulting in increase in the protein permeability and gap pressure of blood vessels, causing blood plasma leakage, reduction of blood vessel diameter and improvement in blood viscosity, and finally leading to tumor necrosis through further slowing down in blood stream and blocking in supply of oxygen and nutrients.

VDAs can be divided into ligand targeted VDAs and small molecular VDAs, in which the former consists of a targeting part (e.g., antibodies, peptide or growth factors) and an effector part (which can kill tumors via different mechanisms), and the latter can be further divided into flavones and microtubulin binding agent. Plinabulin (KPU-2, NPI-2358, Chinese name Plinabulin) developed by Nereus Pharmaceuticals Co., Ltd. is a microtubulin binding agent, which is a synthetic derivative of low molecular cyclo-dipeptide Phenylahistin or halimide derived from marine *Aspergillus* sp, and can selectively act. on the neighborhood of colchicine binding site in endothelial microtubulin to inhibit the polymerization of microtubulin, block off microtubule assembly, thereby destroying the cytoskeleton of endothelial cells, inhibiting the blood stream of tumors without damaging the normal blood vessel system.

Plinabulin binds to the neighborhood of colchicine binding site of microtubulin, acting on MM cells, making MM cells stop growing at the early stage of caryomitosis, thereby inducing cell death. Plinabulin also inhibits the formation of microtubule and the migration of endothelial cells and MM cells, resulting in disfunction of the tumor vascular system. Plinabulin can induce the death of cancer cells without affecting the vigor of other normal monuclear cells.

The chemical structural formula of Plinabulin is as below:

The molecular formula of Plinabulin is $C_{19}H_{20}N_4O_2$, the molecular weight is 336.39, the CAS No. is 714272-27-2. It has good stability.

Deuterium is a stable and non-radioactive isotope of hydrogen, with molecular weight of 2.0144. As the content of deuterium in the generated deuterated compound is far higher than the content of 0.015% as in natural world, hence, it can be deemed as a novel compound. Deuteration in drugs improvement is also accepted by United States Patent and Trademark Office, such as deuterated Rimonabant, Mosapride, Oxybutynin and so on have been approved.

Studies indicate that deuterium is the best bioisostere at present in the design of drugs. Under the action of deuterating, the drug efficacy and toxicity difference caused by different populations and genders can be reduced, the individual difference between patients can be reduced, the adverse reaction events can be reduced through reducing harmful metabolites, and genotoxicity can also be reduced, hence, the action of deuterating has been widely applied to human clinical study and pharmacokinetic study in the drug research and development process. At present, there are many international pharmaceutical enterprises engaging in the research and development of new deuterated drugs, and many deuterated drugs have entered into the clinical experiment, such as CTP-347 and CTP-499.

The important characteristic of deuterium is that its shape and volume in drug molecules are basically the same as those in hydrogen. If the hydrogen in the drug molecules is selectively replaced with deuterium, generally, the deuterated drugs will retain the original biological activity and selectivity. It has been proven by experiments that the binding of the carbon-deuterium bond is more stable than that of the carbon-hydrogen bond. The carbon-deuterium bond formed by deuterium carrying neutrons and carbon vibrates at lower frequency, as a result, it is stronger than the carbon-hydrogen bond. Such increase in strength can directly affect the absorption, distribution, metabolism, discharge and other attributes of some drugs, thereby improving the effectiveness, safety and tolerance of drugs. Hence, theoretically, it is considered that if a certain carbon-hydrogen bond to be decomposed in the drug molecules is deuterated to be the corresponding carbon-deuterium bond, the decomposition process will be delayed, making the action time of the deuterated drugs in bodies longer, which leading to a drug with superior effect to the original one.

SUMMARY OF THE INVENTION

The invention aims to provide deuterated dehydrophenylahistin compounds and a preparation method thereof and use thereof in anti-tumor drugs. The deuterated dehydrophenylahistin compounds provided by the invention have the effect of inhibiting tumor cells, and can be used for preparing anti-tumor drugs.

In order to fulfill the purpose of the invention, the following technical solutions are used:

A deuterated dehydrophenylahistin compound having a structure shown as formula (I):

(I)

Wherein, R₁ is a substituent group monosubstituted or polysubstituted on the benzene ring, which is selected from at least one of hydrogen, deuterium, halogen, hydroxyl, methoxyl, amino, phenyl, amino methyl phenyl, C1-C24 alkyl, C2-C24 alkenyl, C2-C24 alkynyl, aryl alkyl, heterocyclic aryl alkyl, C1-C24 acyl, C1-C24 alkoxy, carboxyl, carboxylate, acylamino, N-monosubstituted or N,N-disubstituted acylamino, sulfo, sulphonate, sulphonylamino, N-substituted sulphonylamino, alkoxy, aryl alkoxy, alkyl sulphanyl, cyano, amino, substituted amino, nitro, naphthenic base, cyclo-alkenyl, aryl, substituted aryl, aryl heterocyclic group, aryloxy, aroyl, epoxy group, cycloacyl, aryl sulfenyl or aryl sulfonyl;

R₂ is hydrogen or deuterium, and R₃ is hydrogen or deuterium;

X₁ is oxygen or sulphur;

X₂ is NH, oxygen or sulphur.

Further, the deuterated dehydrophenylahistin compound is specifically, (3Z,6Z)-3-(phenylmethylene-d)-6-((5-(tert-butyl)-1H-imidazol-4-yl)methylene)piperazine-2,5-dione;
(3Z,6Z)-3-(phenyl-2,3,4,5,6-d₅)-methylene-6-((5-(tert-butyl)-1H-imidazol-4-yl)methylene)piperazine-2,5-dione;
(3Z,6Z)-3-(phenyl-2,3,4,5,6-d₅)-methylene-d-6-((5-(tert-butyl)-1H-imidazol-4-yl)methylene)piperazine-2,5-dione;
(3Z,6Z)-3-(phenylmethylene-d)-6-((5-(tert-butyl)-1H-imidazol-4-yl)methylene-d)piperazine-2,5-dione;
(3Z,6Z)-3-(phenyl-2,3,4,5,6-d₅)-methylene-6-((5-(tert-butyl)-1H-imidazol-4-yl)methylene-d)piperazine-2,5-dione;
(3Z,6Z)-3-(phenylmethylene)-6-((5-(tert-butyl)-1H-imidazol-4-yl)methylene-d)piperazine-2,5-dione;
(3Z,6Z)-3-(phenyl-2,3,4,5,6-d₅)-methylene-d-6-((5-(tert-butyl)-1H-imidazol-4-yl)methylene-d)piperazine-2,5-dione;
(3Z,6Z)-3-(4-Fluoro-(phenyl-2,3,5,6-d₄))-methylene-6-((5-(tert-butyl)-1H-imidazol-4-yl)methylene)piperazine-2,5-dione;
(3Z,6Z)-3-(4-Fluoro-(phenyl-2,3,5,6-d₄))-methylene-6-((5-(tert-butyl)-1H-imidazol-4-yl)methylene-d)piperazine-2,5-dione;
(3Z,6Z)-3-(3-fluorobenzylidene)-6-((5-(tert-butyl)-1H-imidazol-4-yl)methylene-d)piperazine-2,5-dione;
(3Z,6Z)-3-(3-benzoylbenzylidene)-6-((5-(tert-butyl)-1H-imidazol-4-yl)methylene-d)piperazine-2,5-dione;
(3Z,6Z)-3-(3-(4-fluorobenzoyl)benzylidene)-6-((5-(tert-butyl)-1H-imidazol-4-yl)methylene-d)piperazine-2,5-dione;
(3Z,6Z)-3-(3-(4-methoxybenzoyl)benzylidene)-6-((5-(tert-butyl)-1H-imidazol-4-yl)methylene-d)piperazine-2,5-dione;
(3Z,6Z)-3-(3-methoxybenzylidene)-6-((5-(tert-butyl)-1H-imidazol-4-yl)methylene-d)piperazine-2,5-dione; or
(3Z,6Z)-3-(3-(trifluoromethyenzydene)-6-((5-(tert-butyl)-1H-imidazol-4-yl)methylene-d)piperazine-2,5-dione.

The invention further provided a deuterium aldehyde intermediate for synthesizing the deuterated dehydrophenylahistin compound, which has the structure shown as the general formula (II):

(II)

X is NH, oxygen or sulphur.

Further, the deuterium aldehyde intermediate is specifically 5-(tert-butyl)-1H-imidazole-4-carbaldehyde-d; 5-(tert-butyl)oxazole-4-carbaldehyde-d or 5-(tert-butyl)thiazole-4-carbaldehyde-d.

The invention further provided a deuterium-containing heterocyclic compound intermediate for synthesizing the deuterated dehydrophenylahistin compound, which has the structure shown as the general formula (III):

(III)

X₁ is oxygen or sulphur, and X₂ is NH, oxygen or sulphur.

Where, the substituent group R is selected from at least one of C1-C24 alkyl, C2-C24 alkenyl, C2-C24 alkynyl, aryl alkyl, heterocyclic aryl alkyl, C1-C24 acyl, sulfonyl, aroyl, cycloacyl and aryl sulfonyl.

Further, the deuterium-containing heterocyclic compound intermediate is specifically:

(Z)-1-acetyl-3-((5-(tert-butyl)-1H-imidazol-4-yl)methylene-d)piperazine-2,5-dione;
(Z)-1-acetyl-3-((5-(tert-butyl)oxazole-4-yl)methylene-d)piperazine-2,5-dione;
(Z)-1-acetyl-3-((5-(tert-butyl)thiazole-4-yl)methylene-d)piperazine-2,5-dione;
(Z)-1-benzoyl-3-((5-(tert-butyl)-1H-imidazol-4-yl)methylene-d)piperazine-2,5-dione;
(Z)-1-allyl-3-((5-(tert-butyl)-1H-imidazol-4-yl)methylene-d)piperazine-2,5-dione;
(Z)-1-methylsulfonyl-3-((5-(tert-butyl)-1H-imidazol-4-yl)methylene-d)piperazine-2,5-dione; or (Z)-1-tosyl-3-((5-(tert-butyl)-1H-imidazol-4-yl)methylene-d)piperazine-2,5-dione.

The invention provides a preparation method for the deuterated dehydrophenylahistin compound, which comprises the following steps:

(1) Carrying out reduction and oxidation reactions of the aldehyde intermediate a to obtain a deuterium aldehyde compound b, wherein the aldehyde intermediate a and the deuterium aldehyde compound b have the following structural formulas:

a b (2) the first condensation reaction: carrying out a condensation reaction of diacetyl diketopiperazine and the aldehyde intermediate a or the deuterium aldehyde compound b to form a heterocyclic compound c or a deuterium-containing heterocyclic compound d;

The heterocyclic compound c or the deuterium-containing heterocyclic compound d has the following structural formulas:

c d (3) the second condensation reaction, carrying out a condensation reaction of the heterocyclic compound c or the deuterium-containing heterocyclic compound d and aldehyde for the second condensation reaction to form the deuterated dehydrophenylahistin compound, wherein the aldehyde for the second condensation reaction is benzaldehyde, deuterated benzaldehyde or a benzaldehyde derivative with the substituent group on the benzene ring, a deuterated benzaldehyde derivative with the substituent group on the benzene ring.

Further, the aldehyde intermediate a is imidazole formaldehyde, and the deuterium aldehyde compound b is deuterated imidazole formaldehyde.

Further, in the step (1), the preparation method for the deuterium aldehyde compound b comprise: allowing 5-tert-butyl-1H-imidazole-4-formaldehyde to be reduced by $NaBD_4$ and oxidized by manganese dioxide to obtain 5-tert-butyl-1H-imidazole-4-deuterated formaldehyde as the deuterium aldehyde compound b.

Further, in the step (2), the preparation method for the deuterium-containing heterocyclic compound d comprises carrying out the condensation reaction of diacetyl diketopiperazine and the deuterium aldehyde compound b in absence of light under the condition of DMF as a solvent, cesium carbonate as base and N,N-dimethylformamide as a solvent to form the deuterium-containing heterocyclic compound d.

The medicinal composition contains the compound and a pharmaceutically acceptable carrier.

The invention finally provides use of the deuterated dehydrophenylahistin compound in preparation of anti-tumor preparations.

The said tumors comprise skin cancer and leukemia.

The invention has the following advantage and technical effect: the invention provides the deuterated dehydrophenylahistin compounds, and the method for synthesizing the compound comprises: carrying out a condensation reaction of diacetyl diketopiperazine and an aldehyde intermediate a or a deuterium aldehyde compound b to form a heterocyclic compound c or a deuterium-containing heterocyclic compound d, and carrying out a condensation reaction of the product and benzaldehyde and a deuterated benzaldehyde compound to form the deuterated dehydrophenylahistin compounds. Meanwhile, the invention further provides a highly efficient deuterium aldehyde intermediate with high deuterated rate and a deuterium-containing heterocyclic intermediate and a synthetic method thereof. The experiment proves that the deuterated dehydrophenylahistin compounds provided by the invention has the effects of affecting the depolymerization of microtubulin and treating refractory solid tumor or lymphoma. The invention provides a method for studying and developing an anti-tumor drugs for the relating compounds.

DETAILED DESCRIPTION OF THE EMBODIMENTS

The technical solution of the invention has been further described in detail in conjunction with the specific embodiment.

The Synthesis of the Known Compound 5-tert-butyl-1H-imidazole-4-formaldehyde (aldehyde Intermediate a):

The synthetic steps are: cyclization to form an oxazole ring in a first step; carrying out heat treatment in formamide to form an imidazole ring, and reduction and oxidation to obtain imidazole aldehyde compounds in a second step. The reaction formula is as below:

The specific preparation process comprises the following steps:

(1) Dissolving ethyl isocyanoacetate (5.8 mL, 53 mmol) in 90 mL of dried tetrahydrofuran, adding DBU (9.5 mL, 63.6 mmol), then slowly adding trimethyl acetic anhydride (12.9 mL, 63.6 mmol), reacting at room temperature overnight, spin-drying the solvent, extracting with ethyl acetate, leaching using 10% sodium carbonate solution and then leaching using 10% citric acid solution, and drying with anhydrous sodium sulfate. Spin-drying the solvent, carrying out column chromatography isolation and purification, petroleum ether:ethyl acetate=15:1, which are used as an eluent, obtaining 10.3 g of oxazole compound, with yield of 99%.

(2) Adding the oxazole compound (8.1 g, 41 mmol) into a 250 mL round bottom flask, then, adding 60 mL of formamide, heating at 165° C. for reacting, adding 10% sodium carbonate after 24 h to quench the reaction, extracting with ethyl acetate, and drying with anhydrous sodium sulfate. Spin-drying the solvent, carrying out column chromatography isolation and purification, dichloromethane:methanol=60:1, which are used as an eluent, obtaining 4.4 g of imidazole compound, with yield of 55%.

(3) Dissolving the imidazole compound (830 mg, 4.2 mmol) in the dried tetrahydrofuran, adding lithium aluminum hydride (479 mg, 12.6 mmol) at −5° C., heating to room temperature after 0.5 h to react for 4 h, adding water to quench, carrying out suction filtration via a sand core funnel, spin-drying the filtrate, and directly carrying out the reaction of the next step. Dissolving the spin-dried reduced product in 20 mL of dried acetone, adding manganese dioxide (3.6 g, 42 mmol), reacting at room temperature overnight, carrying out suction filtration via the sand core funnel, spin-drying the solvent to obtain 351 mg of compound 5-tert-butyl-1H-imidazole-4-formaldehyde, with yield in the two steps of 55%.

The Synthesis of the Known Compound Heterocyclic Intermediate Z)-1-acetyl-3-((5-tert-butyl-1H-imidazole-4-yl)methylene)piperazine-2,5-diketone (heterocyclic compound c):

The preparation method comprises: adding 5-tert-butyl-1H-imidazole-4-formaldehyde (304 mg, 2 mmol), 1,4-diacetyl piperazine-2,5-diketone (792 mg, 4 mmol), DMF (9 mL), and cesium carbonate (977 mg, 3 mmol) into a reaction flask, reacting at room temperature under the protection of nitrogen for 18 hours (TLC detection shows a complete reaction). Pouring the reactant solution into cold water, and solids are separated out, filtering, and obtaining 320 mg of light yellow solids, i.e., (Z)-1-acetyl-3-((5-tert-butyl-1H-imidazole-4-yl)methylene)piperazine-2,5-diketone, with yield of 55%.

The preparation method for the deuterated dehydrophenylahistin compounds comprises the following steps:

(1) The synthesis of the deuterium aldehyde compound b: starting from the aldehyde intermediate a, reducing via NaBD$_4$ and oxidizing via manganese dioxide, and obtaining the deuterium aldehyde compound b,

(2) the first condensation reaction in: carrying out a condensation reaction of diacetyl diketopiperazine (DKP) and the aldehyde intermediate a or the deuterium aldehyde compound b to form a heterocyclic compound c or a deuterium-containing heterocyclic compound d;

(3) the second condensation reaction: carrying out a condensation reaction of the heterocyclic compound c or the deuterium-containing heterocyclic compound d and a second aldehyde in absence of light to form the deuterated dehydrophenylahistin compound, wherein the second aldehyde is benzaldehyde, deuterated benzaldehyde or a benzaldehyde derivative with the substituent group on the benzene ring, a deuterated benzaldehyde derivative with the substituent group on the benzene ring.

EXAMPLE 1

Preparation of 5-(tert-butyl)-1H-imidazole-4-carbaldehyde-d (deuterium aldehyde compound b), as Show in the Following Figure The specific process for preparing the compound comprises the following step:

5-(tert-butyl)-1H-imidazole-4-carbaldehyde (304 mg, 2 mmol) was weighed and added into a dry and round bottom flask with a volume of 50 mL, and nitrogen was aerated for protection. anhydrous EtOH (5 mL) and NaBD$_4$ (420 mg, 10 mmol) was added into the reaction flask under nitrogen. The resultant mixture was reacted overnight at room temperature. To the quenching reaction, 10 mL water was added. The organic phase was extracted by ethyl acetate. The product was spin-dryed and to be used for the next step directly. 10 mL acetone and MnO$_2$ (1.7 g, 20 mmol) was added, and reaction was carried out overnight at room temperature. Carrying out suction filtration via the sand core funnel, spin-drying the solvent, carrying out column chromatography isolation and purification to obtain off-white solid of 5-tert-butyl-1H-imidazole-4-carbaldehyde-d (199 mg, 1.3 mmol), with yield of 65%.

$^1$H NMR (400 MHz, DMSO-d6) δ 6.97 (s, 1H), 6.66 (s, 1H) 1.05 (s, 9H); MS (ESI) m/z 154.10 (M+H)$^+$ (calcd for C$_8$H$_{12}$DN$_2$O 154.10).

EXAMPLE 2

Preparation of (Z)-1-acetyl-3-((5-(tert-butyl)-1H-imidazol-4-yl)methylene-d)piperazine-2,5-dione (deuterium-containing heterocyclic compound d), as Show in the Following Figure

The specific process for preparing the compound comprises: putting 5-(tert-butyl)-1H-imidazole-4-carbaldehyde-d (306 mg, 2 mmol), 1,4-diacetylpiperazine-2,5-dione (792 mg, 4 mmol), anhydrous MgSO$_4$ (800 mg), DMF (9 mL) and Cs$_2$CO$_3$ (977 mg, 3 mmol) into a reaction flask, and allowing them to react for 18 h at room temperature under nitrogen. The reaction was monitored by TLC until the reaction was complete. The reaction solution was poured into cool water to precipitate solid. And then filtering to obtain 306 mg off-white solid of (Z)-1-acetyl-3-((5-(tert-butyl)-1H-imidazol-4-yl)methylene-d)piperazine-2,5-dione with yield of 52.58%.

$^1$H NMR (400 MHz, DMSO-d6) δ 12.37 (s, 1H), 12.00 (s, 1H), 7.85 (s, 1H), 4.31 (s, 2H), 2.48 (s, 3H), 1.39 (s, 9H); MS (ESI) m/z 292.14 (M+H)$^+$ (calcd for $C_{14}H_{18}DN_4O_3$ 292.14).

EXAMPLE 3

Preparation of (3Z,6Z)-3-(phenyl-2,3,4,5,6-d$_5$)-methylene-6-((5-(tert-butyl)-1H-imidazol-4-yl)methylene-d)piperazine-2,5-dione (compound 1), as Show in Figure The specific process for preparing the compound comprises: putting (Z)-1-acetyl-3-((5-(tert-butyl)-1H-imidazol-4-yl)methylene-d)piperazine-2,5-dione (250 mg, 0.86 mmol), benzal-2,3,4,5,6-d$_5$-dehyde (191 mg, 1.72 mmol), anhydrous MgSO$_4$ (350 mg), DMF (8 mL) and Cs$_2$CO$_3$ (420 mg, 1.29 mmol) into a reaction flask, and allowing them to react at 45° C. for 24 h under nitrogen. The reaction was monitored by TLC until the reaction was complete. The reaction solution was poured into cool water to precipitate yellow solid. And then filtering to obtain filter cake, which was washed by water and a mixture of petroleum ether and ethyl acetate (8:1) successively. The filter cake was dissolved in a mixture of anhydrous EtOH and AcOEt. Insolubles were filtered off, and the filtrate was evaporated in vacuum to yield 140 mg yellow compound 1 with yield of 47.54%.

$^1$H NMR (400 MHz, DMSO-d6) δ 12.31 (s, 1H), 12.22 (s, 1H), 9.98 (s, 1H), 7.83 (s, 1H), 6.74 (s, 1H), 1.37 (s, 9H); MS (ESI) m/z 343.2045 (M+H)$^+$ (calcd for $C_{19}H_{15}D_6N_4O_2$ 343.2036).

EXAMPLE 4

Preparation of (3Z,6Z)-3-(phenylmethylene-d)-6-((5-(tert-butyl)-1H-imidazol-4-yl)methylene-d)piperazine-2,5-dione (compound 2), as Show in Figure The specific process for preparing the compound comprises: putting (Z)-1-acetyl-3-((5-(tert-butyl)-1H-imidazol-4-yl)methylene-d)piperazine-2,5-dione (200 mg, 0.69 mmol), benzaldehyde-d (147 mg, 1.38 mmol), anhydrous MgSO$_4$ (280 mg), DMF (5 mL) and Cs$_2$CO$_3$ (336 mg, 1.03 mmol) in DMF (5 mL) into a reaction flask, and allowing them to react at 45° C. for 22 h under nitrogen. The reaction was monitored by TLC until the reaction was complete. The reaction solution was poured into cool water to precipitate yellow solid. Then filtering to obtain filter cake, which was washed by water and a mixture of petroleum ether and ethyl acetate (8:1) successively. The filter cake was dissolved in a mixture of anhydrous EtOH and AcOEt. Insolubles were filtered off, and the filtrate was evaporated in vacuum to yield 75 mg yellow compound 2 with yield of 32.26%.

$^1$H NMR (400 MHz, DMSO-d6) δ 12.31 (s, 1H), 12.22 (s, 1H), 10.00 (s, 1H), 7.83 (s, 1H), 7.52 (d, J=4 Hz, 2H), 7.39 (t, J=8 Hz, 2H), 7.32 (t, J=8 Hz, 1H), 1.38 (s, 9H); MS (ESI) m/z 339.1788 (M+H)$^+$ (calcd for $C_{19}H_{19}D_2N_4O_2$ 339.1785).

EXAMPLE 5

Preparation of (3Z,6Z)-3-(phenylmethylene)-6-((5-(tert-butyl)-1H-imidazol-4-yl)methylene-d)piperazine-2,5-dione (compound 3), as Show in Figure The specific process for preparing the compound comprises: putting (Z)-1-acetyl-3-(tert-butyl)-1H-imidazol-4-yl)methylene-d)piperazine-2,5-dione (150 mg, 0.51 mmol), benzaldehyde (109 mg, 1.03 mmol), anhydrous MgSO$_4$ (210 mg), DMF (5 mL) and Cs$_2$CO$_3$ (420 mg, 1.29 mmol) in DMF (5 mL) into a reaction flask, and allowing them to react at 45° C. for 21 h under nitrogen. The reaction was monitored by TLC until the reaction was complete. The reaction solution was poured into cool water to precipitate yellow solid. And then filtering to obtain filter cake, which was washed by water and a mixture of petroleum ether and ethyl acetate (8:1). The filter cake was dissolved in a mixture of anhydrous EtOH and AcOEt. Insolubles were filtered off, and the filtrate was evaporated in vacuum to yield 63 mg compound 3 with yield of 36.65%.

$^1$H NMR (400 MHz, DMSO-d6) δ 12.31 (s, 1H), 12.22 (s, 1H), 10.00 (s, 1H), 7.84 (s, 1H), 7.52 (d, J=8 Hz, 2H), 7.39 (t, J=8 Hz, 2H), 7.32 (t, J=8 Hz, 1H), 6.73 (s, 1H), 1.37 (s, 9H); MS (ESI) m/z 338.1715 (M+H)$^+$ (calcd for $C_{19}H_{20}DN_4O_2$ 338.1722).

EXAMPLE 6

Preparation of (3Z,6Z)-3-(phenylmethylene-d)-6-((5-(tert-butyl)-1H-imidazol-4-yl)methylene)piperazine-2,5-dione (compound 4), as Show in Figure The specific process for preparing the compound comprises: putting (Z)-1-acetyl-3-((5-(tert-butyl)-1H-imidazol-4-yl)methylene)piperazine-2,5-dione (290 mg, 1 mmol), benzaldehyde-d (214 mg, 2 mmol), anhydrous MgSO$_4$ (900 mg), DMF (8 mL) and Cs2CO$_3$ (261 mg, 0.8 mmol) into a reaction flask, and allowing them to react at 45° C. until the reaction was complete under nitrogen. The reaction solution was poured into cool water and extracted with dichloromethane (DCM). The solvent was concentrated in vacuo to dry. The concentrate was stirred and pulped in a mixture of petroleum ether and ethyl acetate (8:1), and was filtered. The filter cake was dried to yield 183 mg yellow compound 4 with yield of 54.43%.

$^1$H NMR (400 MHz, DMSO-d6) δ 12.33 (s, 1H), 12.25 (s, 1H), 10.05 (s, 1H), 7.85 (s, 1H), 7.53 (d, J=4 Hz, 2H), 7.43 (t, J=8 Hz, 2H), 7.32 (t, J=8 Hz, 1H), 6.85 (s, 1H), 1.38 (s, 9H); MS (ESI) m/z 338.1715 (M+H)$^+$ (calcd for C$_{19}$H$_{20}$DN$_4$O$_2$ 338.1722).

EXAMPLE 7

Preparation of (3Z,6Z)-3-(phenyl-2,3,4,5,6-d$_5$)-methylene-6-((5-(tert-butyl)-1H-imidazol-4-yl)methylene)piperazine-2,5-dione (compound 5), as Show in Figure The specific process for preparing the compound comprises: putting (Z)-1-acetyl-3-((5-(tert-butyl)-1H-imidazol-4-yl)methylene)piperazine-2,5-dione (300 mg, 1.03 mmol), benzal-2,3,4,5,6-d5-dehyde (230 mg, 2.07 mmol), DMF (14 mL) and Cs$_2$CO$_3$ (505 mg, 1.55 mmol) in into a reaction flask, and allowing them to react at 80° C. for 246 h under nitrogen. The reaction was monitored by TLC until the reaction was complete. The reaction solution was poured into cool water to precipitate yellow solid. And then filtering to obtain filter cake, which was washed by water and a mixture of petroleum ether and ethyl acetate (8:1) successively. The filter cake was dissolved in a mixture of anhydrous EtOH and AcOEt. Insolubles were filtered off, and the filtrate was evaporated in vacuum to yield 229 mg yellow compound 5 with yield of 50.22%.

$^1$H NMR (400 MHz, CDCl$_3$) δ 12.40 (s, 1H), 9.33 (s, 1H), 8.11 (s, 1H), 7.60 (s, 1H), 7.03 (m, 2H), 1.47 (s, 9H); MS (ESI) m/z 342.1984 (M+H)$^+$ (calcd for C$_{19}$H$_{16}$D$_5$N$_4$O$_2$ 342.1973).

EXAMPLE 8

Preparation of (3Z,6Z)-3-(phenyl-2,3,4,5,6-d$_5$)-methylene-d-6-((5-(tert-butyl)-1H-imidazol-4-yl)methylene)piperazine-2,5-dione (compound 6), as Show in Figure The specific process for preparing the compound comprises: putting (Z)-1-acetyl-3-((5-(tert-butyl)-1H-imidazol-4-yl)methylene)piperazine-2,5-dione (290 mg, 1 mmol), benzal-2,3,4,5,6-d5-dehyde-d (224 mg, 2 mmol), anhydrous MgSO$_4$ (900 mg), DMF (10 mL) and Cs$_2$CO$_3$ (261 mg, 0.8 mmol) in into a reaction flask, and allowing them to react at 45° C. for 25 h until the reaction was complete (TLC detection) under nitrogen. The reaction solution was poured into cool water to precipitate yellow solid and extracted with dichloromethane (DCM). The solvent was concentrated in vacuo to dry. The concentrate was stirred and pulped in a mixture of petroleum ether and ethyl acetate (8:1), and was filtered. The filter cake was dried to yield 240 mg yellow compound 6 with yield of 70.17%.

$^1$H NMR (400 MHz, DMSO-d6) δ 12.33 (s, 1H), 12.25 (s, 1H), 10.04 (s, 1H), 7.85 (s, 1H), 6.85 (s, 1H), 1.38 (s, 9H); MS (ESI) m/z 342.2033 (M+H)$^+$ (calcd for C$_{19}$H$_{15}$D$_6$N$_4$O$_2$ 343.2036).

EXAMPLE 9

Preparation of (3Z,6Z)-3-(phenyl-2,3,4,5,6-d$_5$)-methylene-d-6-((5-(tert-butyl)-1H-imidazol-4-yl)methylene-d)piperazine-2,5-dione (compound 7), as Show in Figure The specific process for preparing the compound comprises: putting (Z)-1-acetyl-3-((5-(tert-butyl)-1H-imidazol-4-yl)methylene-d)piperazine-2,5-dione (250 mg, 0.86 mmol), benzal-2,3,4,5,6-$d_5$-dehyde-d (191 mg, 1.72 mmol), anhydrous $MgSO_4$ (350 mg), DMF (8 mL) and $Cs_2CO_3$ (420 mg, 1.29 mmol) into a reaction flask, and allowing them to react at 45° C. for 24 h under nitrogen. The reaction was monitored by TLC until the reaction was complete. The reaction solution was poured into cool water to precipitate yellow solid. And then filtering to obtain filter cake, which was washed by water and a mixture of petroleum ether and ethyl acetate (8:1) successively. The filter cake was dissolved in a mixture of anhydrous EtOH and AcOEt. Insolubles were filtered off, and the filtrate was evaporated in vacuum to yield 138 mg yellow compound 7 with yield of 47%.

$^1$H NMR (400 MHz, DMSO-d6) δ 12.30 (s, 1H), 12.22 (s, 1H), 10.00 (s, 1H), 7.83 (s, 1H), 1.37 (s, 9H); MS (ESI) m/z 344.2096 (M+H)$^+$ (calcd for $C_{19}H_{14}D_7N_4O_2$ 344.2098).

EXAMPLE 10

Preparation of (3Z,6Z)-3-(4-Fluoro-(phenyl-2,3,5,6-$d_4$))-methylene-6-((5-(tert-butyl)-1H-imidazol-4-yl)methylene)piperazine-2,5-dione (compound 8), as Show in Figure The specific process for preparing the compound comprises: putting (Z)-1-acetyl-3-((5-(tert-butyl)-1H-imidazol-4-yl)methylene)piperazine-2,5-dione (300 mg, 1.03 mmol), 4-fluoro-benzal-2,3,5,6-$d_4$-dehyde (265 mg, 2.07 mmol), DMF (6 mL) and $Cs_2CO_3$ (505 mg, 1.55 mmol) into a reaction flask, and allowing them to react at 80° C. for 5 h under nitrogen. The reaction was monitored by TLC until the reaction was complete. The reaction solution was poured into cool water to precipitate yellow solid. And then filtering to obtain filter cake, which was washed by water and a mixture of petroleum ether and ethyl acetate (8:1). The filter cake was dissolved in a mixture of anhydrous EtOH and DCM. Insolubles were filtered off, and the filtrate was evaporated in vacuum to yield 231 mg yellow compound 8 with yield of 62.6%.

$^1$H NMR (400 MHz, DMSO-d6) δ 12.36 (s, 1H), 9.14 (s, 1H), 7.99 (s, 1H), 7.60 (s, 1H), 7.02 (s, 1H), 6.97 (s, 1H), 1.47 (s, 9H); $^{13}$C NMR (400 MHz, DMSO-d6) δ 170.76, 162.93, 160.97, 158.04, 156.74, 140.76, 134.78, 131.48, 129.98, 127.01, 124.23, 113.25, 105.48, 32.35, 31.08 ppm; MS (ESI) m/z 359.1818 (M+H)$^+$ (calcd for $C_{19}H_{16}D_4FN_4O_2$ 359.1816).

EXAMPLE 11

Preparation of (3Z,6Z)-3-(4-Fluoro-(phenyl-2,3,5,6-$d_4$))-methylene-6-((5-(tert-butyl)-1H-imidazol-4-yl)methylene-d)piperazine-2,5-dione (compound 9), as Show in Figure The specific process for preparing the compound comprises: putting (Z)-1-acetyl-3-((5-(tert-butyl)-1H-imidazol-4-yl)methylene-d)piperazine-2,5-dione (250 mg, 0.86 mmol), 4-fluoro-benzal-2,3,5,6-$d_4$-dehyde (220 mg, 1.72 mmol), anhydrous $MgSO_4$ (350 mg), DMF (8 mL) and $Cs_2CO_3$ (420 mg, 1.29 mmol) into a reaction flask, and allowing them to react at 45° C. for 24 h under nitrogen. The reaction was monitored by TLC until the reaction was complete. The reaction solution was poured into cool water to precipitate yellow solid. And then filtering to obtain filter cake, which was washed by water and a mixture of petroleum ether and AcOEt (8:1). The filter cake was dissolved in a mixture of EtOH and ethyl acetate. Insolubles were filtered off, and the filtrate was evaporated in vacuum to yield 144 mg yellow compound 9 with yield of 46.59%.

$^1$H NMR (400 MHz, DMSO-d6) δ 12.30 (s, 1H), 12.22 (s, 1H), 10.11 (s, 1H), 7.83 (s, 1H), 6.72 (s, 1H), 1.37 (s, 9H); MS (ESI) m/z 360.1886 (M+H)$^+$ (calcd for $C_{19}H_{15}D_5FN_4O_2$ 360.1879).

TABLE 1

The structure and chemical name of the compounds obtained in example 3-11

| Compounds | Structure | Chemical name |
|---|---|---|
| Compound 1 | | (3Z,6Z)-3-(phenyl-2,3,4,5,6-$d_5$)-methylene-6-((5-(tert-butyl)-1H-imidazol-4-yl)methylene-d)piperazine-2,5-dione |

TABLE 1-continued

The structure and chemical name of the compounds obtained in example 3-11

| Compounds | Structure | Chemical name |
| --- | --- | --- |
| Compound 2 | | (3Z,6Z)-3-(phenylmethylene-d)-6-((5-(tert-butyl)-1H-imidazol-4-yl)methylene-d)piperazine-2,5-dione |
| Compound 3 | | (3Z,6Z)-3-(phenylmethylene)-6-((5-(tert-butyl)-1H-imidazol-4-yl)methylene-d)piperazine-2,5-dione |
| Compound 4 | | (3Z,6Z)-3-(phenylmethylene-d)-6-((5-(tert-butyl)-1H-imidazol-4-yl)methylene)-piperazine-2,5-dione |
| Compound 5 | | (3Z,6Z)-3-(phenyl-2,3,4,5,6-$d_5$)-methylene-6-((5-(tert-butyl)-1H-imidazol-4-yl)methylene)-piperazine-2,5-dione |
| Compound 6 | | (3Z,6Z)-3-(phenyl-2,3,4,5,6-$d_5$)-methylene-d-6-((5-(tert-butyl)-1H-imidazol-4-yl)methylene)-piperazine-2,5-dione |
| Compound 7 | | (3Z,6Z)-3-(phenyl-2,3,4,5,6-$d_5$)-methylene-d-6-((5-(tert-butyl)-1H-imidazol-4-yl)methylene-d)-piperazine-2,5-dione |

TABLE 1-continued

The structure and chemical name of the compounds obtained in example 3-11

| Compounds | Structure | Chemical name |
|---|---|---|
| Compound 8 | | (3Z,6Z)-3-(4-Fluoro-(phenyl-2,3,5,6-$d_4$))-methylene-6-((5-(tert-butyl)-1H-imidazol-4-yl)-methylene)piperazine-2,5-dione |
| Compound 9 | | (3Z,6Z)-3-(4-Fluoro-(phenyl-2,3,5,6-$d_4$))-methylene-6-((5-(tert-butyl)-1H-imidazol-4-yl)-methylene-d)piperazine-2,5-dione |

EXAMPLE 12

Experiment of Blood Plasma Metabolic Stability In-vitro

The preparation of 10 μmol/mL of Plinabulin (dehydro-phenylahistin) solution: to 10 μL of 1 mg/mL solution, 990 μL of methanol water (1:1) was added to dilute the solution to form a 10 μg/mL solution, to 337.3 μL of 10 μg/mL solution, 662.7 μL of methanol water (1:1) solution was added, thus 1 mL of dehydro-phenylahistin solution at the concentration of 10 μmol/L was prepared. The above operations are carried out in absence of light.

The preparation of Wistar rat plasma: for a 200 g rat, blood was extracted from the heart, carried out anticoagulation with cheparin sodium, and centrifuged at temperature of 4° C. at 8000 r/min for 10 min, and blood plasma was taked.

Figure 1:
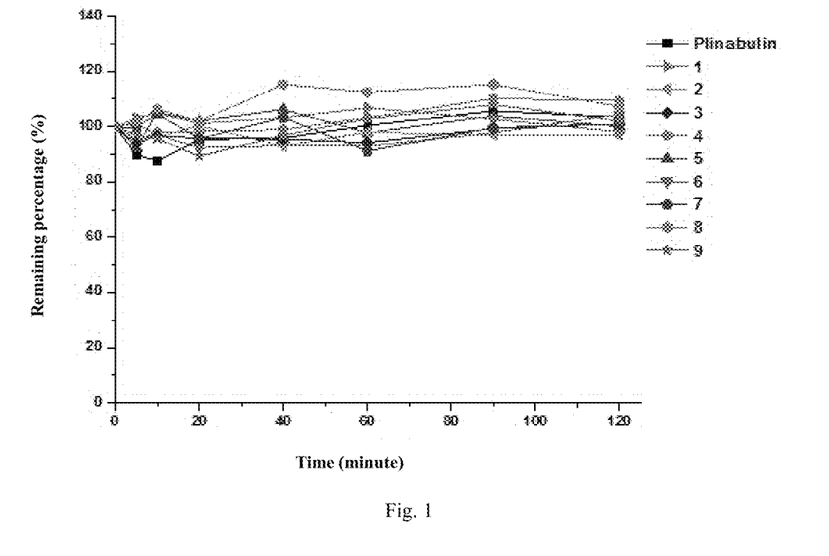
FIG. 1 indicates the metabolic stability of the compounds 1-9 of the invention in blood plasma.

In a 200 μL incubation system, 180 μL blood plasma and 20 μL 10 μmol/L test samples was added sequentially into a 96-well plate. The samples was mixed homogeneously, then put into a water bath oscillator at temperature of 37° C. to incubate, and 300 μL of acetonitrile termination buffer containing the interior label (acetonitrile solution of propranolol with concentration of 100 ng/mL) was added respectively at 0, 5, 10, 20, 40, 60, 90 and 120 min. The mixed solution for reaction centrifuged for 15 min at temperature of 4° C. at 14000 rpm, supernate was carefully taken to a sample introduction bottle, and the residual content of each compound was detected via LC-MS, and the result is shown in FIG. 1. The experimental result of FIG. 1 indicates that the synthesized deuterated series compounds have the stability in blood plasma similar with that of dehydro-phenylahistin as control.

EXAMPLE 13

Experiment of Liver Microsome Metabolic Stability In-vitro

The preparation of solution:
(1) The preparation of $K_2HPO_4$ buffer solution: dissolving 5.7055 g $K_2HPO_4$ in 500 mL tri-distilled water, and adjusting pH to 7.4 using HCl, and the concentration is 50 mmol/L. (2) The liver microsomes (concentration is 20 mg/mL) of rats—the final concentration of incubation is 0.5 mg/mL; (3) the preparation of the standard solution of the compounds to be tested—diluting with reaction buffer to 2 μM, adding 100 μL into each cell, with final concentration of 1 μM. (4) The preparation of NADPH: weighing 10.42 mg NADPH, adding 2.5 mL of $K_2HPO_4$ buffer solution for dissolving, with concentration of 5 mmol·$L^{-1}$. (5) The preparation of acetonitrile solution of propranolol containing the interior label: dissolving 2.20 mg of propranolol in methanol, preparing into a stock solution with concentration of 1 mg·$mL^{-1}$, and diluting with acetonitrile to 100 ng·$mL^{-1}$. The above experiment is carried out in absence of light.

Incubation experiment: the total volume 1 mL, containing 25 μL of microsomes (diluting from 20 mg·$mL^{-1}$ to 0.5 mg·$mL^{-1}$), 200 μL of NADPH (diluting from 5 mmol·$L^{-1}$ to 1 mmol·$L^{-1}$), and 20 μL of compound solution to be tested (diluting from 50 μmol·$L^{-1}$ to 1 μmol·$L^{-1}$), and adding 755 μL of $K_2HPO_4$ buffer solution to 1 mL.

Figure 2:
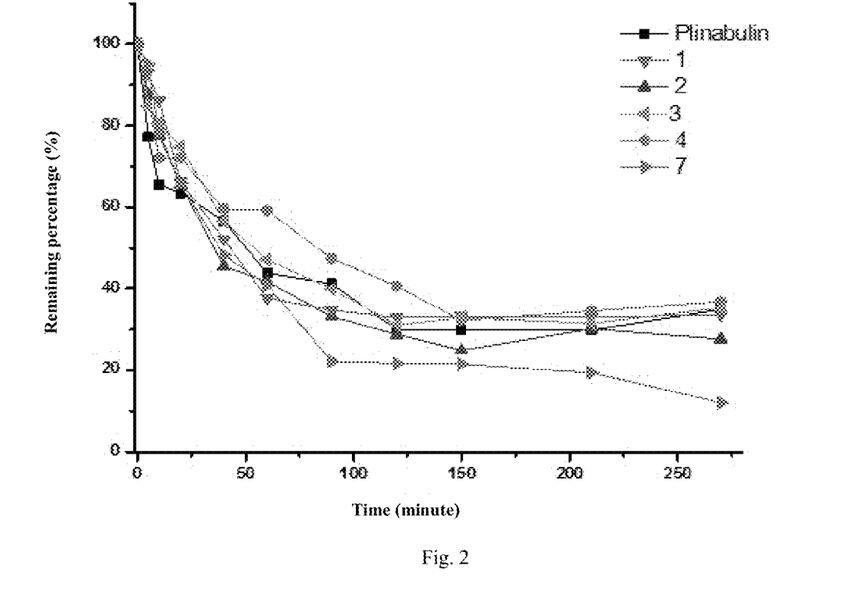
FIG. 2 indicates the metabolic stability of the in-vitro liver microsomes of the compounds 1, 2, 3, 4 and 7 of the invention.

Putting each incubation system in the water bath oscillator at temperature of 37° C. for incubating, extracting 50 μL from the system at 0, 5, 10, 20, 40, 60, 90, 120, 150, 210 and 270 min respectively, and adding 100 μL of acetonitrile containing 100 ng·$mL^{-1}$ of propranolol to terminate the reaction. Duplicating three samples in each group, centrifuging the sample of each termination reaction (4° C., 14000 rpm) for 15 min, taking supernate to be tested by LC-MS/MS for each compound and its residual content, and the result is shown in FIG. 2. The experimental result of FIG. 2 indicates that, in-vitro liver microsomes, the newly synthesized compounds 1, 2, 3, 4 and 7 have the metabolic stability similar with that of dehydro-phenylahistin as control.

EXAMPLE 14

Cell Analysis Method

The inhibition ratio of the selected compounds on tumor cells A431 and Jurkat is measured via the MTT analytical method.

Experiment Materials:

1) Cell strains: human skin cancer cell strain A431 and human acute T cell leukemia cell Jurkat. The ells grow in an RPMI-1640 culture medium and high glucose DMEM (Gibco BRL, Rockville, Md., USA)+10% fetal calf serum (containing 2 mM L-glutamine, penicillin and streptomycin), and putting them into an incubator at 37° C. (5% $CO_2$-95% air) for growing, carrying out digestive passage with 0.25% trypsin, and changing the solution every 1 to 2 days.

2) The dissolution and dilution of compounds: according to the molecular weight and mass of the compounds, preparing into a 10 mM of mother solution respectively using DMSO (SIGMA), and diluting to the required concentration of 100 μM (DMSO content≤3‰) with the RPMI-1640 culture medium. Storing the diluted drugs at temperature of −20° C.

3) RPMI 1640 cell culture medium, Gibco company; fetal calf serum, Hyclone company; cell dissociation solution, 0.25% Trypsin+0.02% EDTA 4) MTT solution, fully dissolving MTT dry powder (Sigma) using PBS to prepare 5 mg/ml solution, filtering via a 0.22 m millipore filter and packaging, and storing at temperature of −20° C.

Experiment Steps:

1) Cell inoculation: Taking cells in the logarithmic phase, after digestion with pancreatin, the cells disperse into single cells, counting, adjusting cell suspension to $8.0\times10^4$ cells/mL, inoculating in the 96-well plates with 180 μL in each well, and making the amount of the inoculated cells is $4.0\times10^3$ cells/well. After cell attachment, adding the fresh culture media containing compounds with different concentrations respectively, making the concentrations of the compounds reach 12.5 nM and 6.25 nM, setting 3 duplicate wells for each concentration, operating in absence of light, and adjusting the content of DMSO in each concentration to be consistent.

2) After drug incubation for 72 h, adding 20 μL of MTT (3-[4,5-dimethylthiazol-2-yl]-2,5-diphenyltetrazolium bromide, Sigma; 5 mg/mL) into each well, incubating in a incubator for 4 h, removing supernate, adding 150 μL of DMSO into each well for dissolving, and measuring absorbancy at 570 nm using the microplate reader. According to the formula: Inhibition ratio=$[(A_{570\ control\ well} - A_{570\ administration\ well})/A_{570\ control\ well}]\times 100\%$, to calculate the inhibition ratio of each concentration, and the result is shown in the table 2.

TABLE 2

Tumor inhibition ratio of compounds on 2 kinds of human cell strains at different drug concentrations

| Serial number | A431 | | Jurkat | |
|---|---|---|---|---|
| | Concentration (nM) | Inhibition ratio (%) | Concentration (nM) | Inhibition ratio (%) |
| Plinabulin | 12.5 | 91.81 | 12.5 | 79.69 |
| | 6.25 | 63.25 | 6.25 | 13.75 |
| Compound 1 | 12.5 | 95.04 | 12.5 | 86.46 |
| | 6.25 | 80.37 | 6.25 | 79.91 |
| Compound 2 | 12.5 | 94.11 | 12.5 | 79.65 |
| | 6.25 | 72.11 | 6.25 | 9.11 |
| Compound 3 | 12.5 | 93.79 | 12.5 | 86.09 |
| | 6.25 | 76.55 | 6.25 | 57.68 |
| Compound 4 | 12.5 | 91.85 | 12.5 | 82.33 |
| | 6.25 | 53.90 | 6.25 | 16.04 |
| Compound 5 | 12.5 | 66.00 | 12.5 | 16.86 |

TABLE 2-continued

Tumor inhibition ratio of compounds on 2 kinds of human cell strains at different drug concentrations

| Serial number | A431 | | Jurkat | |
|---|---|---|---|---|
| | Concentration (nM) | Inhibition ratio (%) | Concentration (nM) | Inhibition ratio (%) |
| Compound 6 | 12.5 | 79.28 | 12.5 | 73.40 |
| | 6.25 | 16.17 | 6.25 | 7.70 |
| Compound 7 | 12.5 | 87.73 | 12.5 | 64.49 |

Note:
A431- human skin cancer cell strain; Jurkat human acute T cell leukemia cell.
Plinabulin (dehydro-phenylahistin) is positive control.

The experimental result of Table 2 indicates that the compounds 1, 2, 3, 4, 5, 6 and 7 have the activity of inhibiting tumors, which is close to that of the positive control Plinabulin (dehydro-phenylahistin), in which the inhibition ratios of the compounds 1, 2 and 3 on A431 and Jurkat cell strain at the concentration of 6.25 nM are higher than that of Plinabulin (dehydro-phenylahistin), indicating the compounds prepared by the invention have the obvious activity of inhibiting tumors, and particularly for skin cancer and acute T cell leucocythemia.

EXAMPLE 15

High Content Imaging Analysis System

I. Experiment Scheme

Plinabulin (dehydro-phenylahistin) is used as positive control, and concentration is set as 12.5 nM. According to the data in earlier-stage, 3 kinds of samples are selected, i.e., compounds 1, 2 and 3. The concentrations of all samples are set as 12.5 nM. According to the experiment method for specific immunofluorescent staining (Alexa 488), the effect of the compounds 1, 2 and 3 on the expression of intracellular microtubulin of human epidermal carcinoma A431 is detected via the high content imaging analysis system.

Experiment Materials:

1) Cell strain: human epidermal carcinoma cell strain A431

2) Culture medium: high glucose DMEM+10% fetal calf serum

3) Trypsin: trypsin powder+disodium ethylenediamine tetraacetic acid (EDTA)

4) Paraformaldehyde: analytically pure

5) Triton X-100: purity>98%

6) Tubulin antibody: Mouse, Santa Cruz Biotechnology

7) DyLight 488-goat anti mouse IgG

Experiment Steps:

1) Taking cells in the logarithmic phase, after digestion with pancreatin, the cells disperse into single cells counting, inoculating in the 96-well plates at $1.2\times10^4$ cells/well, putting at temperature of 37° C., culturing in a 5% $CO_2$ incubator for 24 h until cell attachment.

2) After cell attachment, for experiment group, adding the fresh culture medium containing compounds with different concentrations respectively into each well, making the concentrations of the compounds reach 12.5 nM, and setting 3 duplicate wells for each concentration. In the control group, adding a solvent DMSO with equimultiple diluting, selecting Plinabulin (dehydro-phenylahistin) as a positive drug, setting 3 duplicate wells in each group, and culturing in an incubator at temperature of 37° C. under 5% $CO_2$ saturated humidity for 24 h.

Figure 3:
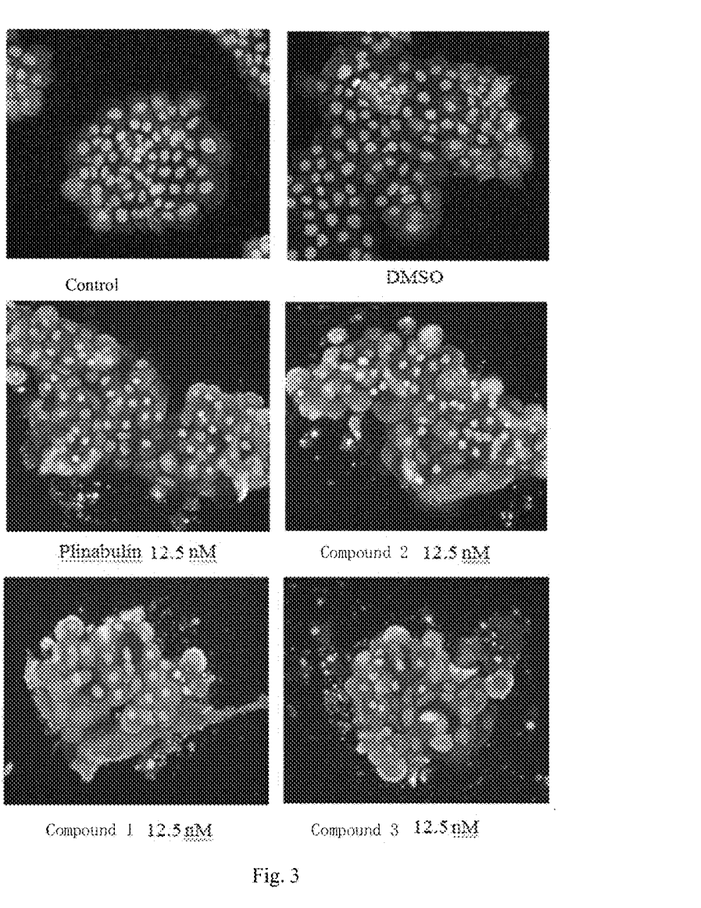
FIG. 3 indicates the effect of Plinabulin (dehydro-phenylahistin) and deuterated analogue compounds 1, 2 and 3 thereof on A431 cell microtubulin.

3) Absorbing the culture medium after 24 h, and washing with PBS for 3 times; fixing with 4% paraformaldehyde for 30 min, absorbing paraformaldehyde, and washing with PBS for 3 times; sealing with 0.3% Triton X-100 and 5% BSA for 30 min, absorbing, and washing with PBS for 3 times; adding Tubulin antibody (mouse antibody, diluting in a ratio of 1:200), and staying overnight at temperature of 4° C.; absorbing, and washing with PBS for 3 times; adding DyLight 488-goat anti mouse IgG (diluting in a ratio of 1:1000), and placing at room temperature for 90 min 4) Photographing analysis of high content imaging analysis system II. Detection Results The detection results are shown in FIG. 3. The blank group and the DMSO control group have no effect on cells. The microtubulin which is the constituent part of cytoskeleton is distributed in the cells uniformly in a diverging form, and after Alexa488 staining, it can be observed that green fluorescence is distributed in the cells uniformly.

Figure 4:
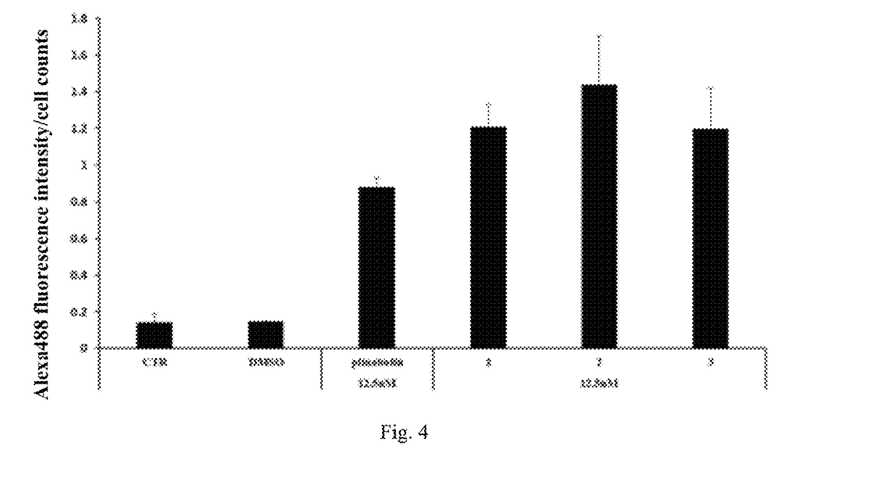
FIG. 4 indicates the effect of Plinabulin (dehydro-phenylahistin) and deuterated analogue compounds 1, 2 and 3 thereof on the fluorescence intensity of A431 cell microtubulin.

The positive control Plinabulin (dehydro-phenylahistin) is a known small-molecular compound that can be acted on microtubulin, the Alexa488 stained fluorescence intensity of microtubulin in the cells is obviously enhanced, and there presents a phenomenon of aggregation in microtubulin and a significant change in cellular morphology (FIG. 3). After the compounds 1, 2 and 3 as samples act on A431 cells for 24 h, the Alexa488 stained fluorescence intensity of microtubulin in the cells is obviously enhanced, and there presents a phenomenon of aggregation in microtubulin and a significant change in cellular morphology. According to the data statistics of Hommeny software, as shown in FIG. 4, compared with the blank group and the control group, the Alexa488 fluorescence intensity after using the compounds 1, 2 and 3 as samples is obviously enhanced, and compared with the positive control, the compounds 1, 2 and 3 as samples are higher than the positive control in the effect.

A series of deuterated dehydrophenylahistin compounds are prepared in the preparation method provided by the invention. The blood plasma metabolic stability experiment, the in-vitro liver microsome metabolic stability experiment, the experiment of the inhibition ratio on tumor cells, the experiment of the effect on the expression of microtubulin in the tumor cells and other experiments are further carried out. The experiment results can prove that the deuterated dehydrophenylahistin compounds of the invention has obvious inhibiting effect on skin cancer and leukemia cells, and has high metabolic stability, hence, they can be used in preparing drugs for treating cancer, and have good market.

The above examples are only used for explaining the technical solution of the invention rather than limitation. Although the invention is subjected to detailed description by referring to the above examples, those skilled in the art can still amend the technical solution in the examples or make identical replacement on part of technical features. Such amendments or replacements do not make the essence of the corresponding technical solution break go away from the spirit and scope of the technical solution claimed for protection in the invention.

The invention claimed is:

1. A compound selected from the group consisting of:
(3Z,6Z)-3-(phenyl-2,3,4,5,6-d$_5$)-methylene-6-((5-(tert-butyl)-1H-imidazol-4-yl)methylene-d)piperazine-2,5-dione; and
(3Z,6Z)-3-(phenylmethylene)-6-((5-(tert-butyl)-1H-imidazol-4-yl)methylene-d)piperazine-2,5-dione.

2. A compound, which is
(Z)-1-acetyl-3-((5-(tert-butyl)-1H-imidazol-4-yl)methylene-d)piperazine-2,5-dione.

3. A preparation method for the compound of claim 1, comprising the following steps:
(1) reacting an aldehyde intermediate a with a deuterated reducing agent to provide an intermediate, and then oxidating the intermediate with an oxidating agent to obtain a deuterium aldehyde compound b;

(2) a first condensation reaction: reacting diacetyl diketopiperazine with the aldehyde intermediate a or the deuterium aldehyde compound b to form a heterocyclic compound c or a deuterium-containing heterocyclic compound d;

(3) a second condensation reaction: reacting the heterocyclic compound c or the deuterium-containing heterocyclic compound d with aldehyde for the second condensation reaction to form the compound of claim 2;

-continued wherein the aldehyde for the second condensation reaction is benzaldehyde, deuterated benzaldehyde or a benzaldehyde derivative with a substituent group(s) on the benzene ring, a deuterated benzaldehyde derivative with a substituent group(s) on the benzene ring;

wherein $R_1$, $R_2$ and $R_3$ are each independently hydrogen or deuternium; n is 1, 2, 3, 4 or 5.

4. The method according to claim 3, wherein the preparation method for the deuterium aldehyde compound b in step (1) is: reducing 5-tert- butyl-1H-imidazole-4-formaldehyde with $NaBD_4$ and oxidating with manganese dioxide to obtain 5-tert-butyl-1H-imidazole-4-deuterated formaldehyde as the deuterium aldehyde compound b.

5. The method according to claim 3, wherein the preparation method for the deuterium-containing heterocyclic compound d in step (2) comprises: condensation reacting diacetyl diketopiperazine and deuterium aldehyde compound b in absence of light under the condition of DMF as a solvent, cesium carbonate as base and N,N-dimethylformamide as a solvent to form the deuterium-containing heterocyclic compound d.

6. A medicinal composition comprising an effective amount of the compound according to claim 1 and a pharmaceutically acceptable carrier.

7. A method for treating a tumor in a subject in need thereof, comprising administrating to the subject an effective amount of a compound according to claim 1, wherein the tumor is selected from the group consisting epidermoid carcinoma and acute T cell leukemia.

8. The method of claim 7, wherein the tumor is epidermoid carcinoma.

9. The method of claim 7, wherein the tumor is acute T cell leukemia.

* * * * *